United States Patent
Alei et al.

[11] Patent Number: 6,027,479
[45] Date of Patent: Feb. 22, 2000

[54] MEDICAL APPARATUS INCORPORATING PRESSURIZED SUPPLY OF STORAGE LIQUID

[75] Inventors: Philip E. Alei, Carlsbad; David K. Wong, Del Mar; Joseph Y. Lucisano, San Diego; Daniel Glazerman, San Diego; David Buse, San Diego, all of Calif.

[73] Assignee: Via Medical Corporation, San Diego, Calif.

[21] Appl. No.: 09/032,752

[22] Filed: Feb. 27, 1998

[51] Int. Cl.[7] ................................................. A61M 37/00
[52] U.S. Cl. ................................................. 604/131
[58] Field of Search ........................ 604/134, 135, 604/138, 152, 151, 131, 132, 133; 600/345, 368

[56] References Cited

U.S. PATENT DOCUMENTS

| | | | |
|---|---|---|---|
| D. 354,347 | 1/1995 | Knute et al. ................. | D24/108 |
| 4,337,769 | 7/1982 | Olson . | |
| 4,573,968 | 3/1986 | Parker ........................... | 604/67 |
| 4,596,558 | 6/1986 | Smith et al. . | |
| 4,627,554 | 12/1986 | Leibinsohn . | |
| 4,842,576 | 6/1989 | Lysaght et al. .............. | 604/134 |
| 5,106,374 | 4/1992 | Apperson et al. ........... | 604/131 |
| 5,109,850 | 5/1992 | Blanco et al. ................ | 128/635 |
| 5,165,406 | 11/1992 | Wong . | |
| 5,220,920 | 6/1993 | Gharib . | |
| 5,248,300 | 9/1993 | Bryant et al. ................ | 604/131 |
| 5,346,476 | 9/1994 | Elson ............................ | 604/135 |
| 5,421,981 | 6/1995 | Leader et al. ................ | 128/635 |
| 5,599,315 | 2/1997 | McPhee . | |
| 5,758,643 | 6/1998 | Wong et al. .................. | 128/632 |

FOREIGN PATENT DOCUMENTS

| | | |
|---|---|---|
| 195 37 271 A1 | 4/1997 | Germany . |
| WO 98/04191 | 2/1998 | WIPO . |

*Primary Examiner*—Jeffrey A. Smith
*Assistant Examiner*—Eduardo C. Robert
*Attorney, Agent, or Firm*—Sheppard, Mullin, Richter & Hampton LLP; James R. Brueggemann

[57] ABSTRACT

An improved apparatus is disclosed for maintaining a medical assembly, e.g., a blood chemistry electrode assembly, filled with a bubble-free storage liquid for an extended storage time period. The apparatus achieves this result by connecting to the assembly a pressurized reservoir that supplies additional storage liquid, to replenish any storage liquid lost due to diffusion from the medical assembly.

15 Claims, 2 Drawing Sheets

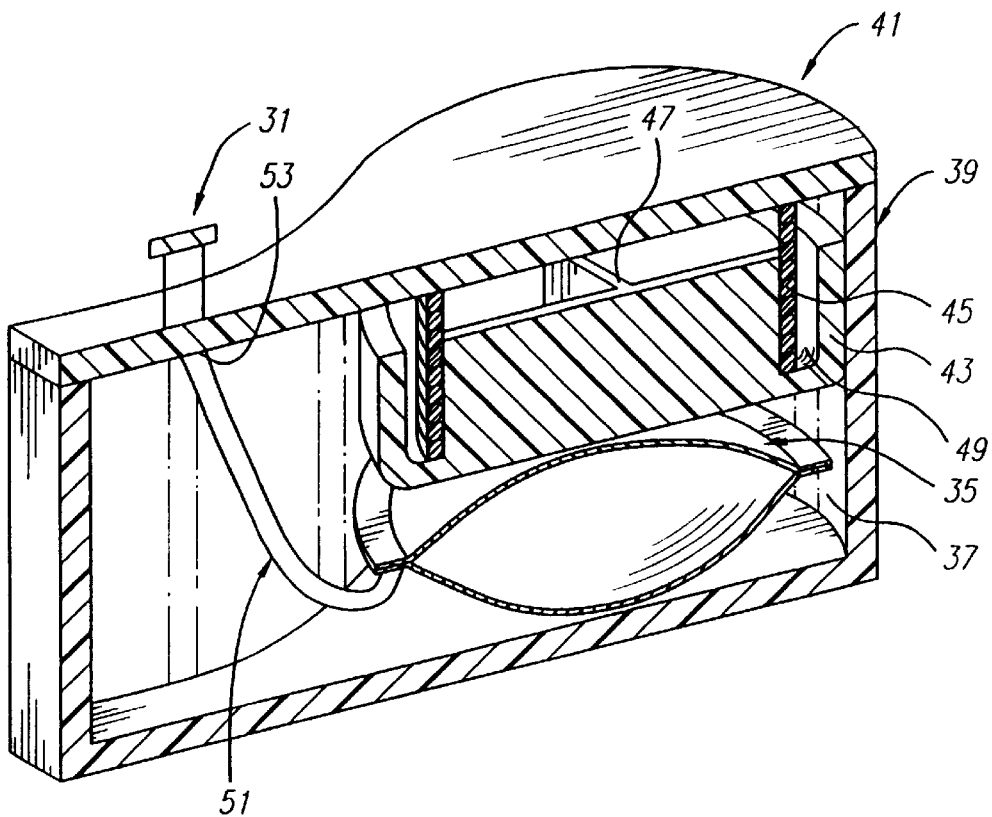
FIG. 4
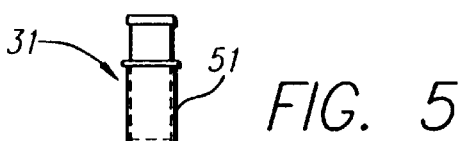
FIG. 5
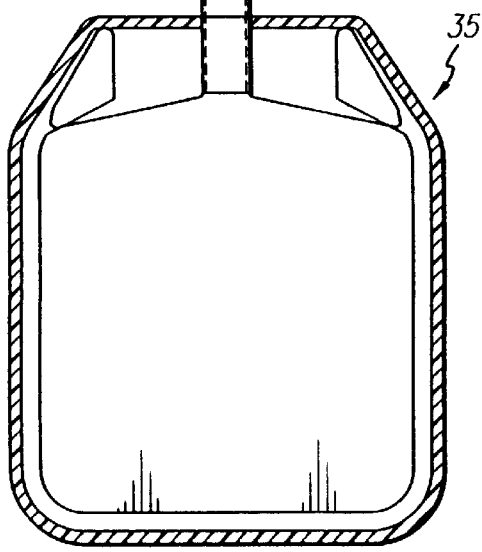
FIG. 6
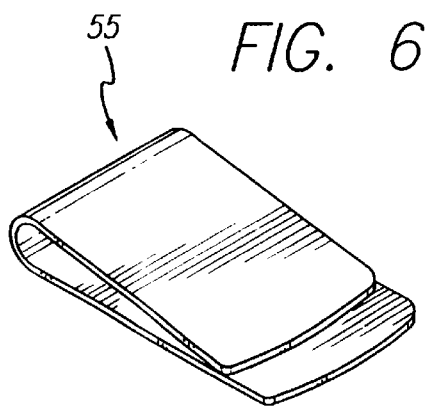

MEDICAL APPARATUS INCORPORATING PRESSURIZED SUPPLY OF STORAGE LIQUID

BACKGROUND OF THE INVENTION

This invention relates generally to medical apparatus for use in extracting liquids from, or injecting liquids into, a living body and, more particularly, to medical apparatus of this kind that are filled with a storage liquid for extended time periods.

Medical apparatus of this particular kind can take many forms, including that of a blood chemistry sensor assembly of the kind disclosed in U.S. Pat. No. 5,165,406, issued in the name of David K. Wong and entitled "Electrochemical Sensor Apparatus and Method." The disclosed blood chemistry sensor assembly includes a rigid plastic housing that defines an elongate test chamber through which passes either blood or a calibration fluid. A plurality of electrochemical sensors are located within the housing, adjacent to the test chamber, each sensor being adapted to measure a separate parameter of the adjacent fluid, e.g., oxygen partial pressure ($pO_2$), carbon dioxide partial pressure ($pCO_2$), glucose, hematocrit, calcium, hydrogen ion (i.e., pH), chloride, potassium, and sodium.

Prior to its being used to measure various parameters of a blood sample, the sensor assembly described briefly above typically is stored for an extended time period, with a storage liquid being located within the assembly's test chamber and with the entire assembly being stored within a sealed container of low permeability. The presence of the storage liquid prevents the sensors from drying out, which could adversely affect their sensing capability, even if subsequently re-wetted. Over time, however, the liquid can diffuse from the test chamber, to at least a limited extent, through the assembly's plastic housing and associated tubing, etc.

The diffusion of liquid from the test chamber can give rise to two problems. First, the resulting negative pressure can draw air or other gas into the test chamber, to form bubbles in the remaining liquid. These gas bubbles can contribute to drying of the sensors, which adversely affects the sensors' performance, even if the bubbles are flushed out prior to use. Further, the diffusion of liquid from the test chamber can change the composition of the remaining liquid. In many circumstances, this change can adversely affect the accuracy of the subsequent sensor measurements.

Other kinds of medical apparatus incorporating liquid-filled chambers that must be stored for extended time periods include ready-mix medication containers configured to directly administer the medication to a patient intravenously, and reagent-containing diagnostic kits for various analytes, etc.

It should, therefore, be appreciated that there is a need for medical apparatus of the kind described above, wherein the apparatus can be reliably stored over an extended time period, without risk of air or other gas entering the apparatus' chamber., and without substantial change to the composition of the storage liquid. The present invention fulfills this need and provides further related advantages.

SUMMARY OF THE INVENTION

The present invention is embodied in an improved medical apparatus for use in extracting a liquid from, and/or injecting a liquid into, a living body, wherein the apparatus is configured to ensure that air and other gases do not enter a liquid-filled chamber while the apparatus is stored over an extended time period. More particularly, the medical apparatus includes a housing that defines the liquid-filled chamber, with various components of the apparatus having at least limited permeability, to allow liquid to diffuse from the housing chamber over time. To compensate for this limited diffusion, the apparatus includes a liquid reservoir in communication with the housing chamber and carrying a storage liquid, and further includes a spring-bias device for pressurizing the liquid reservoir, to pressurize the housing chamber with the storage liquid, such that additional storage liquid is available to replenish liquid that might diffuse from the chamber over time.

In other, more detailed features of the invention, the medical apparatus further includes a one-way check valve located between the liquid reservoir and the housing chamber, for limiting the flow of liquid from the chamber to the reservoir. In addition, the chamber and the reservoir are part of a sterile system, closed to the external environment, and the apparatus further includes an outer container for carrying the housing, the reservoir, and the spring-bias device. Further, the reservoir is sized relative to the housing chamber such that the composition of the storage liquid remains substantially unchanged over time.

In one embodiment of the invention, the medical apparatus' spring-bias device includes a substantially rigid body that defines a cavity sized to carry the liquid reservoir, which takes the form of a flexible bag, and further includes a spring-biased plunger for compressively engaging the flexible bag. In an alternative embodiment, the spring-bias device includes a spring clip sized to compressively grasp opposite sides of such a flexible bag.

The medical apparatus of the invention has particular utility when it takes the form of a sensor apparatus incorporating one or more electrochemical sensors in operative contact with the liquid stored in the housing chamber. Use in the form of a blood chemistry sensor assembly is particularly advantageous.

Other features and advantages of the present invention should become apparent from the following description of the preferred embodiments, taken in conjunction with the accompanying drawings, which illustrate, by way of example, the principles of the invention.

BRIEF DESCRIPTION OF THE DRAWINGS

FIG. 1 is a schematic diagram of a combination infusion fluid delivery and blood chemistry analysis system that incorporates an electrochemical sensor assembly that is part of the preferred embodiment of the invention, shown connected to a blood vessel of a patient's arm.

FIG. 2 is a cross-sectional view of the electrochemical sensor assembly of FIG. 1, showing several electrochemical sensors located adjacent to the assembly's test chamber.

FIG. 3 is a schematic view of the electrochemical sensor assembly of FIG. 1, combined with a pressurized reservoir assembly in accordance with one preferred embodiment of the invention.

FIG. 4 is a sectional isometric view of the pressurized reservoir assembly of FIG. 2, showing a spring-biased platen that compressively engages a flexible bag carrying a supply of storage liquid.

FIG. 5 is a plan view of the flexible bag of FIG. 4, shown with an attached delivery tube and one-way check valve.

FIG. 6 is a perspective view of a spring clip that can be used to compressibly engage a flexible bag to form a pressurized reservoir assembly in accordance with an alternative embodiment of the invention.

DESCRIPTION OF THE PREFERRED EMBODIMENTS

Figure 1:
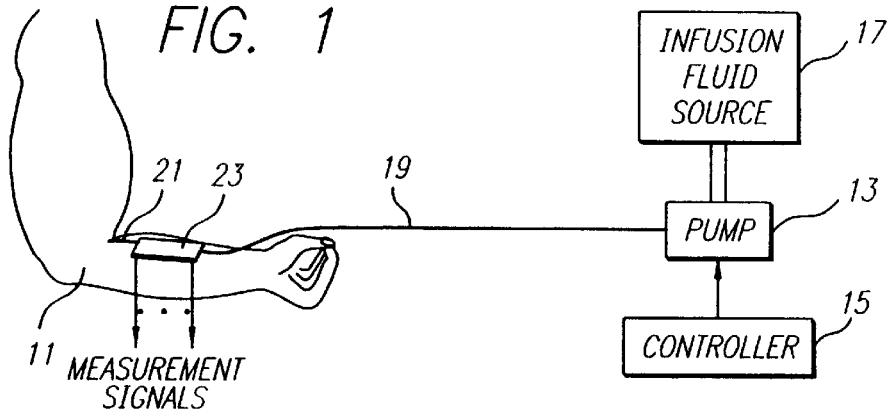
Figure 2:
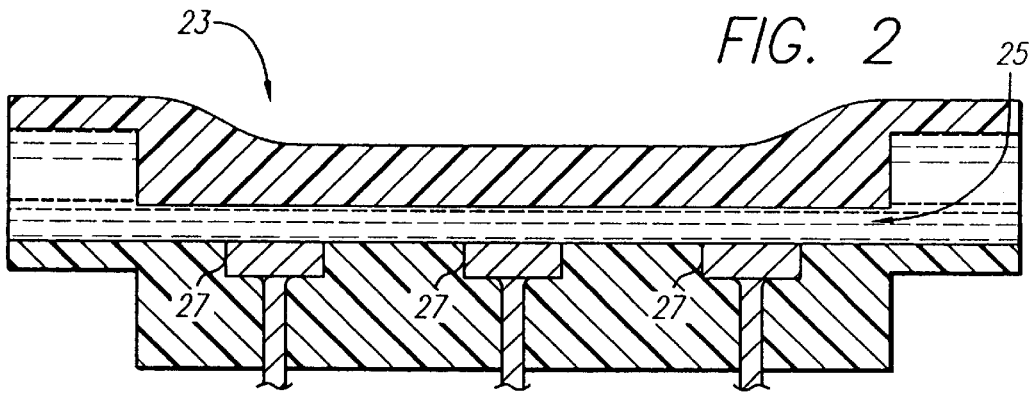

With reference now to the drawings, and particularly to FIGS. 1 and 2, there is shown an infusion fluid delivery and blood chemistry analysis system in use connected to a blood vessel within a patient's arm 11. An infusion pump 13, under the control of a controller 15, pumps an infusion/calibration fluid from a fluid source 17 to the blood vessel via an infusion tube 19 and hollow needle 21. A sensor/electrode assembly 23 is located in the infusion line, the assembly including a test chamber 25 through which the infusion/calibration fluid passes on its way to the patient. Several electrochemical sensors 27 are located within the electrode assembly, immediately adjacent to the test chamber, such that they can measure predetermined parameters of the adjacent fluid.

Periodically, the controller 15 conditions the pump 13 to interrupt its pumping of the infusion/calibration fluid to the patient and, instead, to reverse direction and draw a blood sample from the patient. This blood sample is drawn rearwardly through the infusion tube 19 as far as the electrode assembly 23, to allow the assembly's electrochemical sensors 27 to measure certain parameters of the blood. After the measurements have been completed, the pump reinfuses the blood sample back into the patient and then resumes pumping the infusion/calibration fluid. The sensors are configured to measure parameters such as oxygen partial pressure ($pO_2$), carbon dioxide partial pressure ($pCO_2$), glucose, hematocrit, calcium, hydrogen ion (i.e., pH), chloride, potassium, and sodium.

The electrode assembly 23 normally must be stored for an extended time period before being used to make blood sample measurements. During this storage time, it is important that the electrochemical sensors 27 remain wetted, because dried-out sensors can provide inaccurate measurements, even if re-wetted prior to making their measurements. The electrode assembly, therefore, is stored with a storage liquid filling its test chamber 25. Unfortunately, the plastic materials from which the body of the electrode assembly and the infusion tube are constructed allow at least limited diffusion of the storage liquid from the test chamber. Unless appropriately controlled, this diffusion would lead to a negative pressure within the test chamber, thus drawing air or other gases into the remaining liquid and causing undesired bubbles to be formed.

Figure 3:
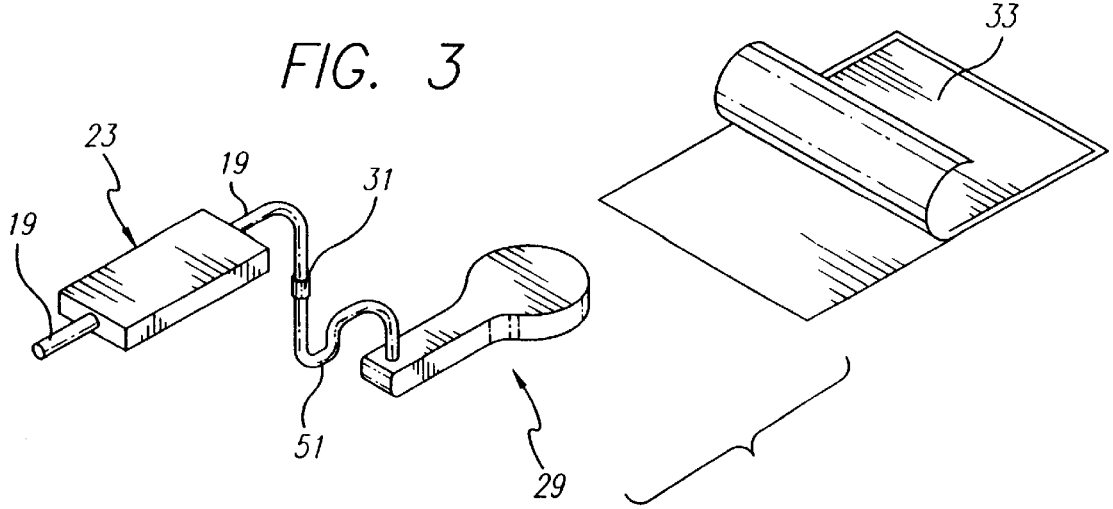

As shown in FIG. 3, this air bubble problem is avoided by storing the electrode assembly 23 with a pressurized reservoir assembly 29, which provides a pressurized supply of storage liquid to replenish whatever liquid is lost through diffusion. The electrode assembly and the pressurized reservoir assembly form a closed, sterile system that carries the storage liquid and isolates the liquid from the external environment. The reservoir assembly incorporates a spring-loaded check valve 31, for coupling directly to a standard luer connector in the infusion line 19 that projects from the electrode assembly. The valve opens only when connected to the mating luer connector, thus allowing the reservoir assembly to be disconnected from the electrode assembly without a loss of the storage liquid. The two assemblies are packaged within a sealed container 33, preferably of low permeability. The reservoir assembly is sized to carry sufficient storage liquid to replenish the amount of liquid expected to be lost due to diffusion over the maximum storage time period.

FIGS. 4 and 5 depict the pressurized reservoir assembly 29 in greater detail. The assembly includes a flexible bag 35 formed from two flat plastic sheets arranged in confronting relationship and heat-sealed around their periphery. The bag is carried in a cavity 37 of a hollow housing 39, and a removable cover 41 encloses the cavity. A molded plastic, cup-shaped platen 43 is positioned between the bag and the cover, and a coil spring 45 urges the platen into compressive engagement with the bag. Cross braces 47 are molded into the platen's top side, to provide rigidity and to define a ring-shaped recess 49 for receiving the coil spring.

A plastic delivery tube 51 extends from one edge of the flexible bag 35 through an opening 53 in the removable cover 41 to the check valve 31. The flexible bag preferably is formed of polypropylene copolymer, with the strength of the peripheral seal being at least 5 pounds per inch, and with the bag able to withstand a pressure of 6 pounds per square inch for at least 48 hours without leakage. The delivery tube preferably includes two coextruded layers, with an outer layer formed of polyolefin and an inner layer formed of polyvinyl chloride (PVC). The check valve preferably is a conventional Halkey-Roberts luer-activated valve, formed of PVC, and it is bonded to the tube using cyclohexanone, with a bond strength of at least 10 pounds.

FIG. 6 depicts a flat metal spring clip 55 that can be used with a flexible bag 35 like that of FIG. 5, to form an alternative embodiment of a pressurized reservoir assembly. The spring clip is sized and configured to slide over the bag and pressurize the storage liquid contained within it. In this embodiment, the bag is formed of a material having low water vapor permeability, to reduce fluid loss.

In other embodiments, not shown in the drawings, the pressurized reservoir assembly can incorporate alternative means for maintaining fluid pressure. Examples of such alternative pressure means include compressed air or other gas, compressible foam, and other extension and compression spring arrangements.

In the preferred embodiments, the flexible bag 35 is substantially less permeable than is the sensor/electrode assembly 23. Because of this, the storage liquid diffuses away from the sensor/electrode assembly faster than it does from the bag. In addition, the bag preferably is sized to carry a substantially greater amount of storage liquid than is stored in the test chamber 25. Consequently, as the storage liquid within the test chamber is replenished with liquid from the bag, its composition remains substantially unchanged. This is a significant improvement over prior systems of this kind, in which the diffusion of liquid from the test chamber sometimes had a significant (and undesired) effect on the composition of the liquid that remains.

It should be appreciated from the foregoing description that the present invention provides an improved apparatus for maintaining a medical apparatus, e.g., an electrochemical sensor assembly, filled with a storage liquid and bubble-free for an extended storage time period. The apparatus achieves this result by connecting to the sensor assembly a pressurized reservoir that supplies additional storage liquid to replenish any storage liquid lost due to diffusion from the medical assembly.

Although the invention has been described in detail with reference only to the presently preferred embodiments, those of ordinary skill in the art will appreciate that various modifications can be made to those embodiments without departing from the invention. Accordingly, the invention is defined only by the following claims.

We claim:

1. Medical apparatus adapted to be stored for an extended time period, the apparatus comprising:
   a housing defining a liquid-filled chamber, wherein the housing is configured such that liquid located within the chamber can escape therefrom over time;
   a sensor carried within the housing, in operative relationship to the chamber, for measuring the concentration of a predetermined parameter of any liquid within the chamber;
   a liquid reservoir communicating with the housing chamber and carrying a storage liquid; and
   a spring-bias device for pressurizing the liquid reservoir, to pressurize the chamber with the storage liquid, such that additional storage liquid is supplied to the chamber as liquid escapes therefrom over time.

2. Medical apparatus as defined in claim 1, and further comprising a one-way check valve located between the liquid reservoir and the housing chamber, for limiting the flow of liquid from the chamber to the reservoir.

3. Medical apparatus as defined in claim 1, wherein:
   the housing chamber and the liquid reservoir define a closed, sterile system; and
   the medical apparatus further comprises an outer container for carrying the housing, the reservoir, and the spring-bias device, the outer container being substantially liquid impermeable.

4. Medical apparatus as defined in claim 1, wherein:
   the liquid reservoir is a liquid-filled flexible bag; and
   the spring-bias device includes
      a substantially rigid body defining a cavity sized to carry the liquid-filled flexible bag, and
      a spring-biased plunger for compressively engaging the liquid-filled flexible bag.

5. Medical apparatus as defined in claim 1, wherein:
   the liquid reservoir is a liquid-filled flexible bag; and
   the spring-bias device includes a spring clip sized to compressively grasp opposite sides of the liquid-filled flexible bag.

6. Medical apparatus as defined in claim 1, wherein the components of the medical apparatus are sufficiently permeable to allow limited escape of the storage liquid therefrom over time and to allow air to be introduced into the chamber over time.

7. Sensor apparatus for sensing the concentration of a predetermined parameter in a liquid, comprising:
   a housing defining a test chamber;
   a sensor carried within the housing, in operative relationship to the test chamber, for measuring the concentration of a predetermined parameter of any liquid located within the test chamber;
   wherein the apparatus is configured such that liquid located within the test chamber can escape therefrom over time;
   a flexible reservoir communicating with the test chamber and carrying a storage liquid; and
   a spring-bias device for compressing the flexible reservoir, to pressurize the test chamber with the storage liquid, such that additional storage liquid is supplied to the test chamber as liquid escapes therefrom over time.

8. Sensor apparatus as defined in claim 7, and further comprising a one-way check valve located between the flexible reservoir and the test chamber, for limiting the flow of liquid from the test chamber to the flexible reservoir.

9. Sensor apparatus as defined in claim 7, wherein:
   the test chamber and the flexible reservoir define a closed, sterile system; and
   the sensor apparatus further comprises an outer container for carrying the housing, the flexible reservoir, and the spring-bias device, the outer container being substantially liquid impermeable.

10. Sensor apparatus as defined in claim 7, wherein the spring-bias device comprises:
    a substantially rigid body defining a cavity sized to carry the flexible reservoir; and
    a spring-biased plunger for compressively engaging the flexible reservoir.

11. Sensor apparatus as defined in claim 7, wherein the spring-bias device comprises a spring clip sized to compressively grasp opposite sides of the flexible reservoir.

12. Sensor apparatus as defined in claim 7, wherein the components of the sensor apparatus are sufficiently permeable to allow limited escape of the storage liquid therefrom over time and to allow air to be introduced into the test chamber over time.

13. A blood chemistry sensor assembly comprising:
    a housing defining a test chamber;
    a plurality of sensors carried within the housing, in operative relationship to the test chamber, for measuring the concentration of predetermined parameters of blood introduced into the test chamber;
    wherein the sensor assembly is stored with a storage liquid in its test chamber;
    and wherein components of the sensor assembly are sufficiently permeable to allow limited escape of the storage liquid from the test chamber over time and to allow air to be introduced into the test chamber over time;
    a flexible bag that carries a supply of storage liquid, in liquid communication with the test chamber; and
    a spring-bias device for pressurizing the flexible bag, such that additional storage liquid is supplied to the test chamber as liquid escapes therefrom over time.

14. A blood chemistry sensor assembly as defined in claim 13, wherein the spring-bias device comprises:
    a substantially rigid body defining a cavity sized to carry the flexible bag; and
    a spring-biased plunger for compressively engaging the flexible bag.

15. A blood chemistry sensor assembly as defined in claim 13, wherein the spring-bias device comprises a spring clip sized to compressively grasp opposite sides of the flexible bag.

* * * * *